United States Patent [19]

Carrabba et al.

[11] Patent Number: 5,255,067
[45] Date of Patent: Oct. 19, 1993

[54] SUBSTRATE AND APPARATUS FOR SURFACE ENHANCED RAMAN SPECTROSCOPY

[75] Inventors: Michael M. Carrabba, Franklin; Martin W. Rupich, Framingham; R. David Rauh, Newton, all of Mass.

[73] Assignee: EIC Laboratories, Inc., Norwood, Mass.

[21] Appl. No.: 621,172

[22] Filed: Nov. 30, 1990

[51] Int. Cl.⁵ .......................... G01J 3/44; G01N 21/65
[52] U.S. Cl. .................................................... 356/301
[58] Field of Search .......................... 356/301, 244, 36

[56] References Cited
U.S. PATENT DOCUMENTS 4,674,878  6/1987  Vo-Dinh ............................ 356/301
4,781,458  11/1988  Angel et al. ....................... 356/301
5,017,007  5/1991  Milne et al. ........................ 356/301

OTHER PUBLICATIONS

Bello et al, *Applied Spectroscopy*, vol. 44, No. 1, Jan. 1990, pp. 63–69.

Primary Examiner—F. L. Evans

[57] ABSTRACT

A substrate and apparatus for qualitatively and quantitatively detecting constituents of an environment by surface enhanced Raman spectroscopy. The substrate is composed of two separate phases: an adsorbing phase which has an affinity for the molecular constituents of interest, and a metallic phase that possesses the specific geometry, chemical and electromagnetic properties required to enhance emission of Raman signal frequencies of adsorbed molecules. An apparatus is provided which includes a monochromatic light source, a means to transmit the desired wavelength from the light source to the surface substrate surface, a means to collect the scattered Raman signal frequencies and transmit them to a detector, and a means to analyze the recorded response.

16 Claims, 7 Drawing Sheets

SUBSTRATE AND APPARATUS FOR SURFACE ENHANCED RAMAN SPECTROSCOPY

This invention was made with Government support under Contract Number N00014-88-C-0661 awarded by the United States Office of Naval Research.

FIELD OF THE INVENTION

This invention relates to the substrates and apparatus which enable the use of surface enhanced Raman spectroscopy for the detection and identification of molecular species.

BACKGROUND OF THE INVENTION

A general need exists for chemical sensors which can be used both to identify and to quantitatively measure a wide range of molecular constituents in a gaseous medium. In the past, the predominant techniques have had relatively low structural specificity, for example, electrochemical or calorimetric detection of oxidizable gases (see, for example, M. J. Madou and S. R. Morrison, *Chemical Sensing with Solid State Devices*, Academic Press, N.Y. (1989)). However, the range of environmental species requiring detection and monitoring has exceeded the capabilities of these instruments. Improved sensors are needed in which the molecular structure of gaseous species giving a positive sensor response can be assigned or confirmed with a high degree of certainty.

A particularly attractive method for detection and identification of unknown molecular species is Raman spectroscopy. Like infrared spectroscopy, the Raman spectrum gives a series of sharp lines which constitute a unique fingerprint of a molecule. These lines correspond to frequencies of molecular vibrations and therefore can be related directly to molecular structure. Raman spectroscopy employs visible light and hence can be used for remote sensing over optical fibers using common visible or near infrared laser sources. In addition, water, which is ubiquitous in most sampling environments, gives only a very weak Raman spectrum and hence would not greatly interfere with detection. Raman is, however, a notoriously insensitive technique requiring nearly neat samples to achieve reasonable signal levels. Raman detection of dilute gas phase species would require an extremely long pathlength, with difficulties of optical alignment and associated ultraclean optics for multiple reflection cells.

When molecules are adsorbed onto some solid substrates, an enhanced Raman signal of the adsorbate is obtained, with up to $10^7$ greater signal intensity than would normally be observed. This phenomenon forms the basis of Surface Enhanced Raman Spectroscopy (SERS). Surfaces which give rise to the enhancement are certain metals such as Ag, Au and Cu; most other metals show no such effect. To maximize the effect, the metal must have a high degree of surface roughness. The latter has been obtained by electrochemical oxidation/reduction of metal surfaces, or by vapor deposition of the metal onto a high roughness substrate.

SERS is typically observed with the substrate in aqueous solution. Organic molecules readily displace water from metal surfaces, acting in some cases to preconcentrate molecules present at high dilution. For this reason, SERS has been proposed as a promising technique for detecting low levels of pollutants in sources of drinking water. However, if the roughened metal substrates are placed in air, they do not readily adsorb foreign molecules present in the gas phase, or the surface becomes saturated with atmospheric gases; thus, the same preconcentration is not obtained. It is for this reason that SERS has not been exploited as a gas phase sensor.

A particular example where high specificity and low detection limits are required is in the aerospace industry, which presently uses large quantities of hypergolic fuels consisting of hydrazine and its derivatives. The toxicity, tumorigenic and explosive properties of the hydrazines necessitate their real-time, low level detection in order to ensure the protection and safety of personnel. Threshold limit values of 100 ppb for hydrazine and 200 ppb for monomethylhydrazine requires portable instrumentation and dosimeters capable of detection of these materials at the 10 to 100 ppb level. However, portable instrumentation based on present state-of-the-art sensor technologies are unable to achieve interference free, real-time detection at the parts per billion level. In addition to the low level sensing, the need exists to sense in real time leaks in the 0–200 ppm range that would be encountered during ground based operations of the space shuttle.

SUMMARY OF THE INVENTION

The primary object of the present invention is to provide a practical means for qualitatively detecting and quantitatively measuring one or more molecular species in a gaseous medium by surface enhanced Raman spectroscopy (SERS).

It is another object of this invention to provide a SERS active substrate that is capable of reproducibly adsorbing the gaseous species of interest.

It is yet another object of this invention to provide an apparatus incorporating the aforesaid SERS active substrate for making spectroscopic measurements of gas phase species, including those remote from the measurement apparatus.

In order to accomplish the objects of the present invention, a two phase substrate is provided. The first phase consists of a SERS-active metal that is a metal with both the appropriate composition and surface morphology to impart SERS activity. The second phase, in intimate contact with the first, serves to interact with the gaseous species. The form of this interaction may be physisorption, chemisorption or direct chemical reaction. The second phase is sufficiently thin and/or porous to bring the adsorbate or product sufficiently close to the surface of the first layer to induce SERS enhancement. The phases may be present as sequential layers or as a porous matrix of the adsorbing phase impregnated with the SERS-active metal phase.

Another aspect of the present invention is to provide an apparatus for conducting spectroscopic measurements of the adsorbate. This apparatus comprises a monochromatic light source, the substrate of this invention, means for transmission of the monochromatic light source to the substrate, optical means for collection and transmission of the scattered Raman signal to a spectrometer or optical filter, and a detector and the necessary electronics for controlling the apparatus and analyzing the collected signal and displaying an output corresponding to the identity and concentration of the gaseous species of interest.

Other objects and advantages of the present invention will become apparent from the following detailed description.

DETAILED DESCRIPTION OF THE INVENTION

The present invention provides a substrate for obtaining surface enhanced Raman spectra of molecular species, and is particularly suited for detection of species initially present in the gas phase. The key component in the invention is a specially prepared SERS surface that will interact with selected species present in the environment leading to their concentration and confinement onto that surface near SERS active sites. Thus, the surface is comprised of a SERS-active metal such as Ag, Au or Cu prepared in a high surface area morphology and then covered by a second material that functions as an adsorbant and/or reactant for the molecular species to be detected. The most readily realized structure of this sort is a roughened metal covered with its own oxide.

Figure 1:
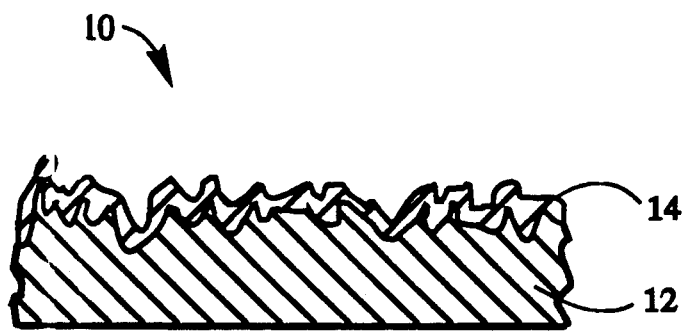
FIGS. 1 and 2 is a cross sectional and detail schematic representations of the two-phase SERS active substrate of this invention comprising a nonporous coating on a SERS-active metal.
Figure 2:
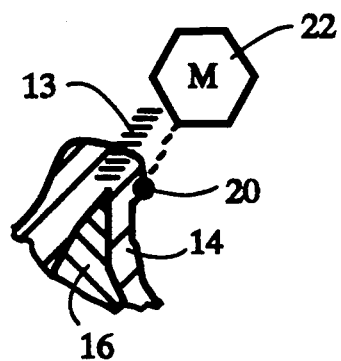
Figure 3:
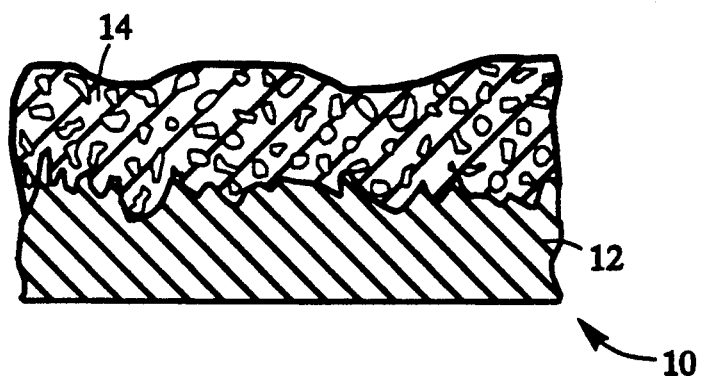
FIGS. 3 and 4 are cross sectional and detail schematic representations of the two-phase SERS active substrate of this invention comprising a porous coating on a SERS-active metal.
Figure 4:
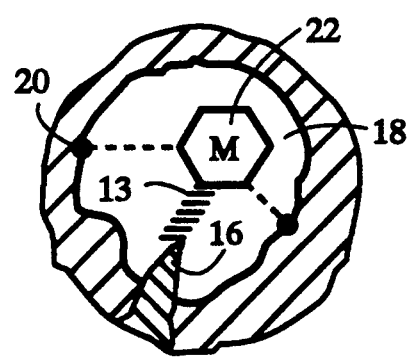

Referring now to FIGS. 1 through 6 are cross-sectional and detail views, not to scale, of bilayer SERS-active substrates 10 which are the subject of this invention. FIG. 1 depicts a SERS-active metal layer 12 with a high degree of microscopic roughness coated with an adsorbing layer 14. In FIG. 2, the coating is shown as being nonporous but sufficiently thin or discontinuous to bring the adsorbing species within the electromagnetic field 13 of the SERS-active sites 16 (shown as sharp metal protrusions). FIGS. 3 and 4 show the coating as a porous layer, which could be used to enhance adsorbancy. The microscopic features (16) of the metal surface which afford SERS activity are shown in FIG. 4 to be in proximity with a pore (18) of the adsorbant. The coatings in FIGS. 2 and 4 are shown to have surface sites (20) which have an affinity for certain molecules (22). These molecules need not have a special affinity for metal features 16, but rather are drawn into their proximity by adsorption at 20.

Figure 5:
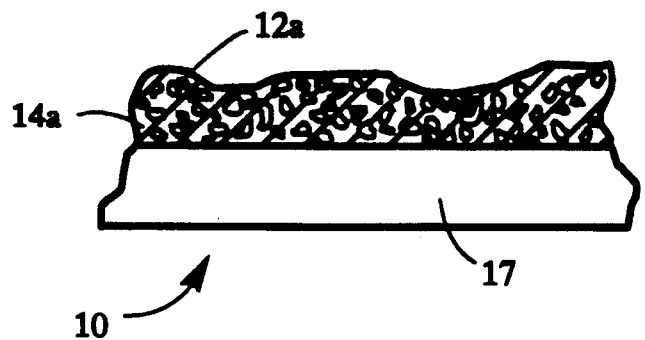
FIGS. 5 and 6 is a cross sectional and detail schematic representations of the two-phase SERS active substrate of this invention comprising a substrate wherein the SERS active phase is dispersed within the adsorbing-/reacting phase.
Figure 6:
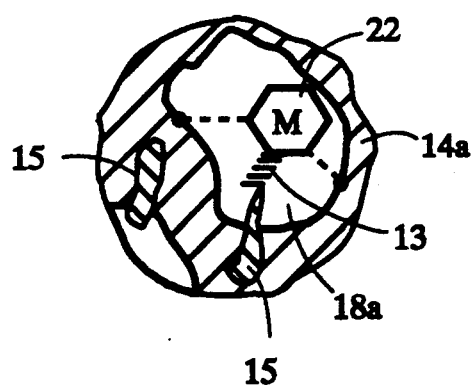

Referring to FIGS. 5 and 6, it is also possible to prepare the two layers such that the SERS-active metal 12a and the adsorbing/reacting layer 14a are interpenetrating, one dispersed within the other. This interpenetrating system may be deposited as a thin ($<10$ μm) or thick ($>10$ μm) onto a suitable support 17. Such dispersed substrates may be conveniently achieved by incorporating a salt of the SERS-active metal in the porous adsorbing material, then by treating the latter with a chemical reducing agent to precipitate metal nuclei or islands 15 at the interior surface of the pore 18a. An example of this procedure is to react porous silver oxide with hydrazine. In this case, SERS-active silver nuclei formed by partial reduction of the oxide matrix.

It should be noted at this point that if the Raman spectrum of the porous precursor material is monitored during the reduction process, the intermediates or products of the reductant/precursor material are frequently observed by their enhanced Raman spectra due to the growing metal nuclei. In these cases, a sensor for the reducing agent itself may be achieved from only the precursor material. For example, silver oxide may be exposed to hydrazine, giving rise to SERS of the hydrazine decomposition intermediates. Exposure of the resulting composite to air will cause the hydrazine products to desorb, leaving an interpenetrating substrate as in FIGS. 5 and 6 which can be used to detect other adsorbants.

The underlying SERS-active metal surface of FIGS. 1 through 4 may be prepared using any one of a number of methods employed in prior art. Metals which are predicted to have high activity for imparting SERS include Ag, Au, Cu, Ni and Pt. It is further observed, and also predicted by some current theories, that the metals have a microroughness on the 1–50 nanometer scale. This roughness may be induced by sequentially oxidizing then reducing the metal in an electrochemical cell. For example, Ag in a Cl electrolyte deposits AgCl on its surface during the oxidation step, then microparticles of Ag metal are produced on the reduction step. An Ag substrate roughened in this way shows high SERS activity, while SERS is absent in an unroughened Ag electrode.

Colloidal suspensions of Ag or Au particles 5–20 nanometers in diameter show SERS activity. These can be case onto a suitable self-supporting substrate, such as filter paper. SERS-active surfaces can also be prepared by physical vapor deposition onto a suitable support under conditions where island or agglomerated morphology is dominant, e.g., by evaporating a metal film onto a cold substrate. Another method is to start with a base substrate with high surface roughness, then to deposit the SERS-active metal onto that surface either electrochemically or by physical or chemical vapor deposition. A variation of the latter process is to deposit the metal onto monodisperse latex microspheres as described by Vo-Dinh, U.S. Pat. No. 4,674,878 (1987). Similarly, various techniques of microlithography can be used to etch regular arrays of posts, pyramids, or other protruding structures into semiconductor surfaces. These then can be used as substrates for depositing SERS-active metals.

The second step in preparing the surface is to deposit the adsorbing or reacting layer. If this second layer is the oxide of the underlying metal, the procedure may be conveniently carried out electrochemically. It is noteworthy that the condition for forming the electrochemical roughening, which produces a surface relatively free of oxide, and for anodic oxide formation are frequently different. Thus, they are carried out under different electrolytic conditions, and typically in different media. For example, Ag is roughened by electrochemical cycling between −600 m V and 200 m V vs. standard calomel electrode (SCE) in 0.1M KCl; the oxide is formed by holding the roughened electrode at a constant positive potential in 1M KOH. Similar two-step electrochemical procedures may be devised for roughening, then forming the anodic oxide of other SERS-active metals. Alternatively, the roughening and oxide growth may be carried out in the same electrolyte, for example, by cycling Ag in 1M KOH solution. The choice of procedure will ultimately be determined by the composition and morphology of the resulting oxide and how those factors influence the adsorbancy or reactivity of the oxide to the species of interest.

In this invention it is important to differentiate "native" oxides, which are present on all metals, from oxides and other coatings produced by "external means". It is the "external means" of deposition which result in coatings having the proper composition and/or morphology to render them active. The "native" oxides that form on roughened metal surfaces by simple exposure to ambient air do not give rise to the effects described herein. Roughened metal substrates coated with such "native" oxides are really what has been assumed to be bare metal in all prior art. "External means" shall be defined as any way of producing coatings which is different from simply exposing the substrate to air. Such "external means" include oxidation at elevated temperatures, electrochemical deposition or anodization, physical vapor deposition such as sputtering, chemical vapor deposition, dipping in a solution containing the coating species, etc. Obviously all coatings which are not composed of the oxide of the underlying metal must be formed by "external means".

Conditions of deposition of the coating may be chosen to yield a porous oxide with a high internal surface area that favors gas absorption. Porous oxides may be formed on the roughened metal substrates by electrochemical deposition or precipitation. These need not be the oxide of the base metal. For example, nickel oxide/hydroxide may be deposited onto a roughened Ag surface by cathodic precipitation of the hydroxide from neutral solutions of nickel salts.

Porous layers may also be formed by physical vapor deposition onto the roughened metal substrates. For example, porous oxides may be deposited onto roughened metal substrates by reactive sputtering from a metal target under high oxygen pressures. Similarly, porous oxides are produced by sputtering or by thermal or electron beam evaporation of oxide sources in the presence of a significant background pressure of water.

Some oxides may be defined as "reactive" with the species of interest, and can be either the oxide of the underlying SERS-active substrate or a foreign oxide. For example, silver oxide is known to exist in two oxidation states that can be interconverted electrochemically. The formulas are approximately designated as AgO and $Ag_2O$. Thus, a SERS-active roughened Ag surface can be oxidized electrochemically and the oxidation state may be specified by the electrochemical potential of oxidation. AgO may be an oxidizing agent for some gas phase materials, while $Ag_2O$ may have reducing properties toward other gaseous moieties. A variety of oxides may be prepared as coating materials which react with oxidizable molecules. The products formed by the reaction are typically a lower valent oxide and adsorbed molecular oxidation products. The original oxide can then be regenerated either by thermal reaction with $O_2$, or by electrochemical anodization. Oxide/reduced oxide pairs that can be made to operate in this way include: $AgO/Ag_2O$; $AuO_2/Au_2O_3$, $Ni_2O_3/NiO, PbO_2/Pb_2O_3, CoO_2/Co_2O_3$, $IrO_2/Ir_2O_3$, $RuO_2/Ru_2O_3$, $RhO_2/Rh_2O_3$, and $CuO/Cu_2O$.

The adsorbing or reactive layer need not be an oxide. For example, organic polymers may be prepared with absorptive or reactive properties. These may be generated on the roughened metal substrates by several possible techniques, e.g., electropolymerization, dipping or casting, photopolymerization and plasma polymerization. Similarly, the second layer may be an organic or inorganic compound with specific adsorptive or reactive properties toward a gas phase species of interest. These may be deposited onto the metal substrate by solution evaporation, for example.

In devising bilayer substrates, the adsorbing/reacting layer may be chosen to interact generally or specifically with gas phase species. Layers with a general affinity for organic species include high surface area carbon, hydrated silica (silica gel), and zeolite molecular sieves. Coating materials with varying degrees of specificity for gaseous molecules have been reviewed for use with quartz crystal microbalance detectors, see J. Hlavay and G. G. Gullbault, "Applications of the Piezoelectric Crystal Detector in Analytical Chemistry", Anal. Chem. 49, 1890–1899 (1977). These coatings include ethylenedinitrotetraethanol, which reacts with $SO_2$, ascorbic acid/silver nitrate mixtures for ammonia, $FeCl_3$ for organophosphorous compounds, anthraquinone disulfonic acid for $H_2S$, triphenyl amine for HCl, and trans-$IrCl(CO)(PPh_3)_2$ for aromatic hydrocarbons.

So-called "conductive polymers" have been shown to have wide ranging properties for modification of reactivity. Some of these polymers may be readily formed by electrochemical oxidation, e.g., onto the underlying SERS-active substrate. In this way, substituted polypyrrole and polythiophenes may be formed by electrochemical oxidation of the respective pyrrole or thiophene monomers. A reactive moiety may be linked covalently to the polymer backbone, or may be incorporated ionically.

Figure 7:
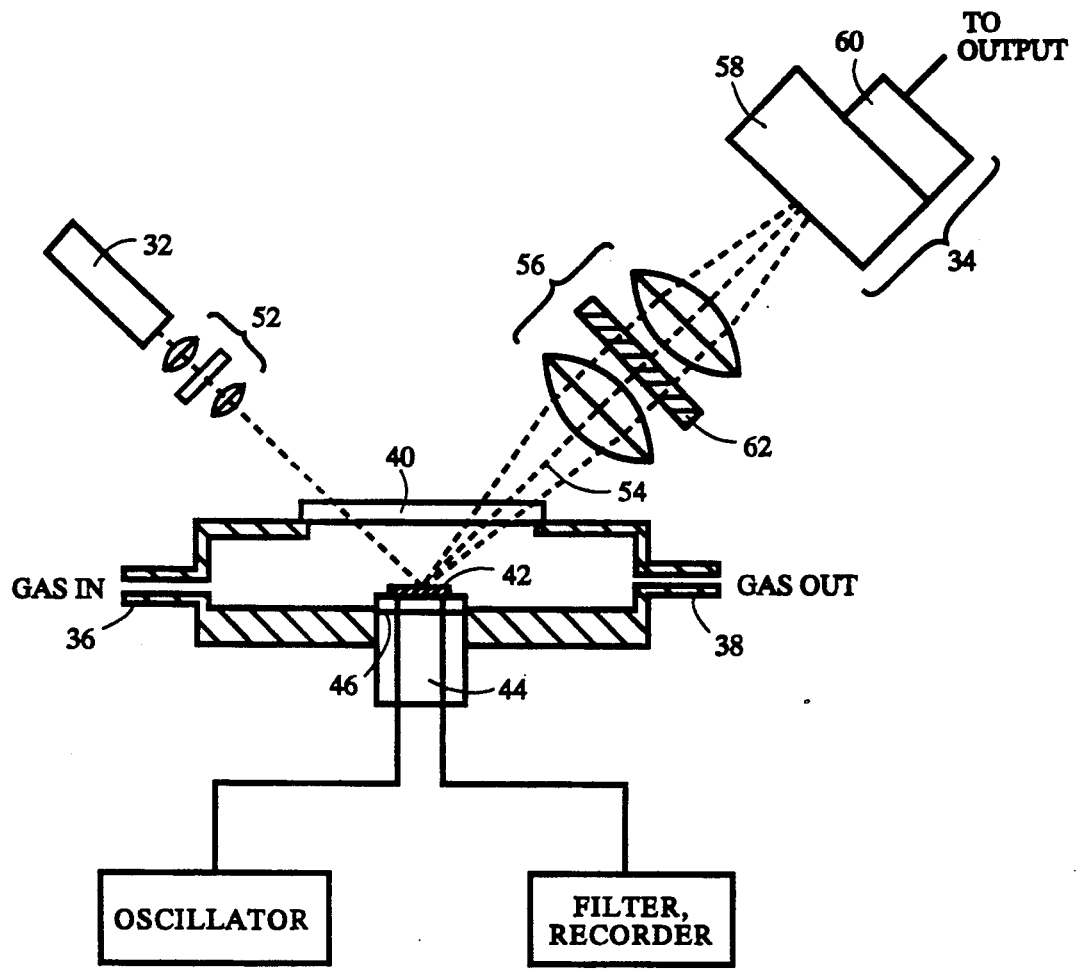
FIG. 7 is a schematic representation of the apparatus within the present invention wherein the SERS-active substrate is incorporated onto a piezoelectric substrate.

An apparatus for measuring gas phase surface enhanced Raman spectra using the bilayer substrate of this invention is shown in FIG. 7. The apparatus consists of three major components: a cell 30 for containing the substrate and flowing gaseous sample; a light source 32 and associated optics for directing the light onto the sample; and 34 a detection system for analyzing the scattered light.

The cell body is suitably fitted with tubes 36 and 38 for inlet and output of the sampled gas. The cell also contains on its front surface a window 40 for exciting Raman scattering, and on its interior back surface the bilayer substrate 42 on a suitable support 44. In one preferred embodiment, the substrate is in thermal contact with a heater for maintaining a constant temperature or regenerating the active surface.

A preferred substrate embodiment in the apparatus is to incorporate it onto the surface of a crystal 46 whose vibrational frequency excited by an alternating voltage is a function of the mass on its surface. Thus, the identity of the adsorbing species could be specified from the SERS spectrum while the amount of adsorbed species could be accurately specified by the crystal vibration frequency. In such a way, the SERS sensor described in this invention could be combined with a mass sensor, variously configured as scanning acoustic wave device, quartz crystal microbalance or other piezoelectric devices.

Referring to FIG. 7, the light source 32 is typically a laser, which delivers a monochromatic beam to the surface 40. The light may be delivered either directly from the laser source, or preferably after collimation, filtration and subsequent focusing with optical components 52 onto the substrate area. The Raman scattering 54 is collected by a lens or lens assembly 56, preferably at an oblique angle with a wide aperture (low f-number) to enable high collection efficiency. The collected light is then focused onto the slit of a monochrometer 58. The grating in the monochrometer may be scanned, and a photoelectric device 60 such as a photomultiplier tube on the output of the monochrometer used to detect the intensity of the Raman scattered light as a function of wavelength. Alternatively, the monochrometer may have a stationary grating, and the spectrum of the scattered light projected onto a diode array, Hadamard transform mask or charge coupled device, positioned at the output aperture. The aforementioned techniques of Raman sampling and detection are summarized by D. L. Gerrard and H. J. Bowley, in "Instrumentation for Raman Spectroscopy", which appears as Chapter 3 in Practical Raman Spectroscopy, D. J. Gardner and P. R. Graves (Eds.), Springer Verlag (1989).

An optional light filter or filters 62 which pass only a limited wavelength range may be inserted in the collection path to discriminate further against light of unwanted frequencies, such as the laser excitation frequency. If it is desirable to monitor only one wavelength region, this filter or filters may be selected to pass only that wavelength and the monochrometer may be eliminated; a single photomultiplier, photodiode, or other light sensitive device is then used as a detector.

In the event of sampling in a remote or hazardous environment, optical fiber probes may be used. Such probes have been described in prior art, see for example, S. D. Schwab and R. L. McCreery, "Versatile, Efficient Raman Sampling with Fiber Optics", Anal. Chem. 56, 2199 (1984). In the present invention, the fiber optic probe bundle would replace the front sampling window in the cell of FIG. 7. The fiber optic probe is then introduced using an adaptor which holds the probe or probe array in fixed orientation with respect to the substrate.

EXAMPLE 1

Silver/Silver Oxide Bilayer Substrate with Organic Vapors

The substrate was prepared starting with 1 mm diameter polycrystalline silver wire. The wire was sealed into a glass capillary along with a thermocouple. A high resistance Ni-Cr wire was then wound around the capillary and the entire assembly sealed into a 4 mm Pyrex tube with a high temperature epoxy. The end of the substrate was then cut so that only the cross section of the silver wire was exposed, followed by polishing in an alumina slurry to produce a mirror-like substrate surface. After polishing, the substrate surface was thoroughly rinsed with doubly distilled water. The substrate was then introduced into an electrochemical cell and roughened by cycling in 0.1M KCl between $-0.6$ and 0.2 V vs. SCE. The potentiostatic cycling was stopped at the cathodic potential limit to ensure reduction of all anodically formed surface AgCl to the (SERS-active) rough Ag metal. The roughened metal surface was then covered with oxide by electrochemical oxidation in 1.0M KOH electrolyte at 0.85 V vs. SCE. The thickness of the oxide layer was limited, through coulometric monitoring, to <100 monolayers to preserve the morphology of the roughened underlying substrate.

Raman spectra of the oxidized substrate were measured using a continuous wave dye laser operating at 575 nm. The sample assembly was incorporated into a Teflon cell of geometry shown in FIG. 7. The sample cell was contained in the sampling compartment of a commercial Raman spectrometer (SPEX Industries, Triplemate), which employed an intensified diode array detector and an optical multichannel analyzer.

Figure 8:
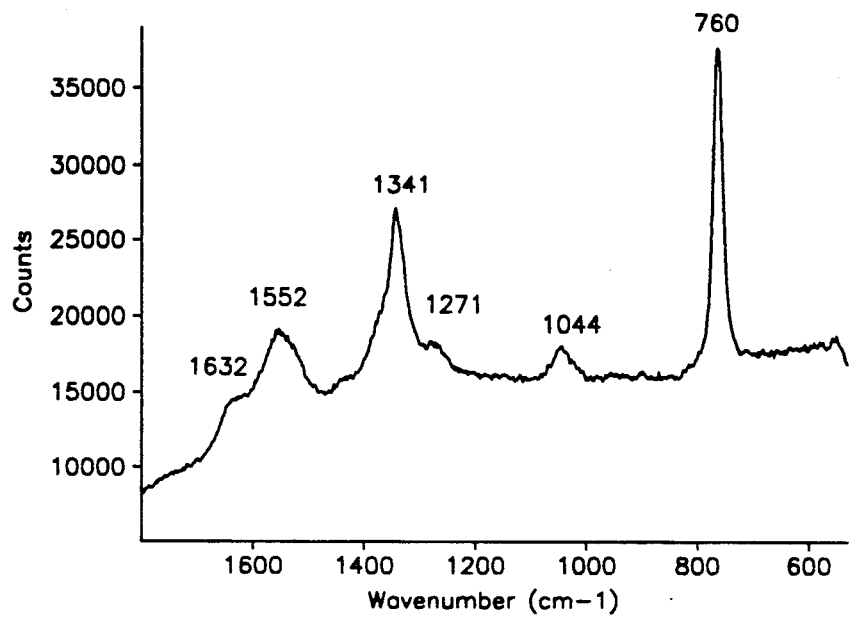
FIG. 8 presents the Surface Enhanced Raman spectrum of formaldehyde vapor adsorbed onto a roughened silver/silver oxide bilayer substrate.
Figure 9:
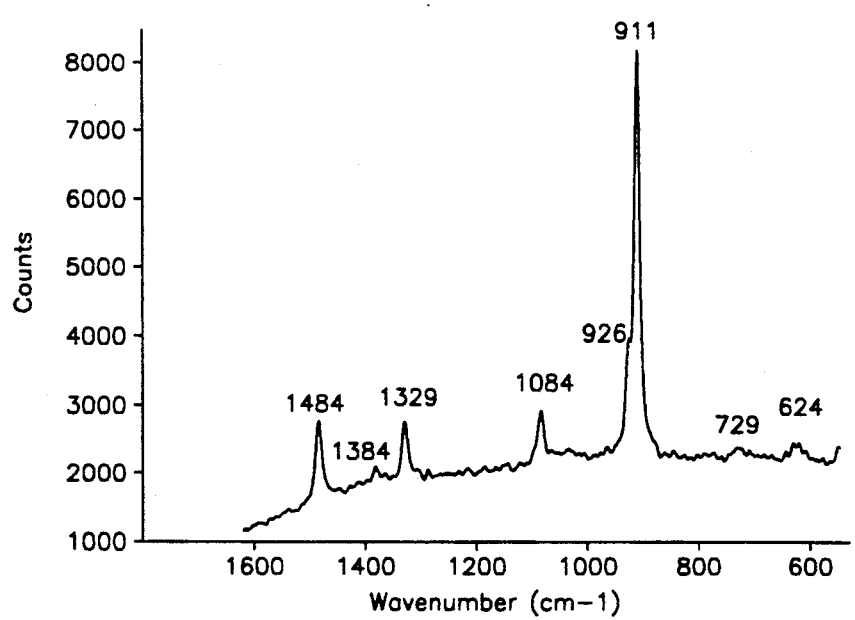
FIG. 9 presents the normal Raman spectrum of pure formaldehyde.

Table 1 summarizes the response of the silver/silver oxide to several organic vapors in air, compared to the roughened silver substrate without the externally formed oxide coating. The Raman spectrum of formaldehyde vapor on silver/silver oxide is shown in FIG. 8. The spectrum is not seen on Ag alone. Since it does not correspond identically to the Raman spectrum of neat formaldehyde, also shown in FIG. 9, the spectrum corresponds to a product of reaction or chemisorption. Hence, silver/silver oxide in this case is an example of a reactive coating on a SERS-active substrate.

EXAMPLE 2

Silver/Silver Oxide as a Hydrazine Sensor

The following experiment demonstrates the utility of the invention for detecting and monitoring hydrazine and other similar hypergolic rocket fuels.

Figure 10:
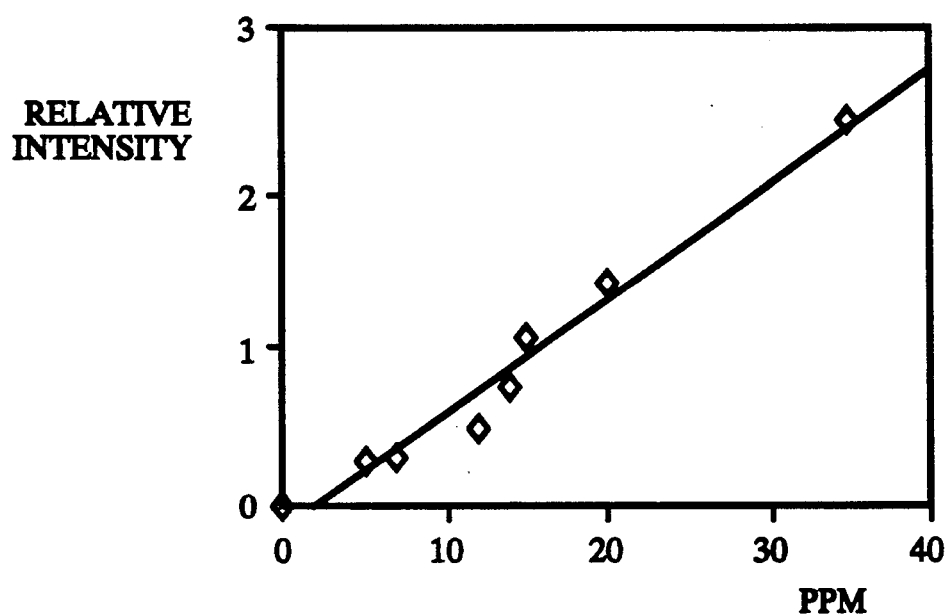
FIG. 10 is a graph showing the intensity of the 940 $cm^{-1}$ hydrazine SERS peak on a silver/silver oxide bilayer substrate as a function of hydrazine concentration in air.

A silver/silver oxide substrate was prepared as in Example 1. Hydrazine-air mixtures were introduced over the substrate. The major peaks associated with the hydrazine were observed at 900-1100 cm$^{-1}$. The lower detection limit was approximately 50 parts per billion. A steady state response was obtained which was proportional to concentration. The surface was regenerated by removing the hydrazine in the gas stream, or by increasing the substrate temperature to $>70°$ C. in the hydrazine-air stream, indicated by the disappearance of the 940 cm$^{-1}$ peak. These experiments indicate a dynamic equilibrium at the substrate so that the sensor can be used either as a continuous monitor or as a sampling device. FIG. 10 shows the signal level at 940 cm$^{-1}$ as a function of hydrazine concentration, indicating that the sensor can be used to determine the concentration of hydrazine. Methyl-substituted hydrazines give similar levels of sensitivity. The positions of the spectral peaks can be used to distinguish the different hydrazine fuel components.

EXAMPLE 3

Ethanol Vapor Detector

The invention can be used as a detector for ethanol in the presence of other vapor species, as indicated by the following experiment. This application would be used in the construction of a breath analyzer for intoxication.

A gold oxide substrate was prepared on a SERS-active Au substrate. The roughened Au underlayer was obtained by multiple electrochemical cycling in 0.1M KCl at 50 mV/sec between voltage limits of $-0.6$ and 1.2 V vs. SCE. The Au oxide film was grown in a 1M H$_2$SO$_4$ electrode by polarizing the electrode at 1.1 V vs.

SCE for 10 min, followed by rinsing with distilled water and drying in flowing air.

Figure 11:
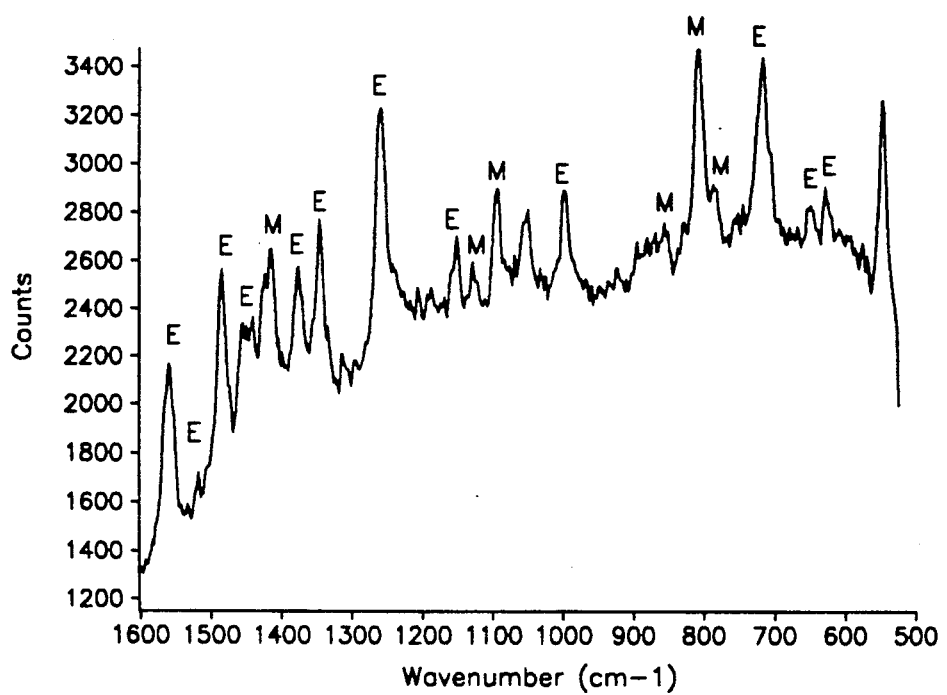
FIG. 11 is the Surface Enhanced Raman Spectrum of a mixture of ethanol and methanol vapor adsorbed onto a roughened gold/gold oxide bilayer substrate.

A highly resolved spectrum of ethanol was observed on the gold oxide substrate, when introduced as a vapor stream in an air diluent. No spectrum of ethanol was observed on the roughened gold itself, due to its lower affinity for polar alcohols. A similarly resolved spectrum was obtained for methanol vapor. FIG. 11 shows the spectrum obtained on gold oxide for a mixed ethanol/methanol vapor stream in an air carrier gas. The peaks associated with the two components may be clearly discerned. The peak positions in this case correspond to those for the pure liquids, indicating a physisorptive equilibrium.

EXAMPLE 4

Sputtered Silver Oxide

A roughened Au substrate was prepared as in Example 3. A layer of silver oxide was then deposited onto the Au by reactive radio frequency sputtering from a pure silver target at an oxygen background pressure of $1.4 \times 10^{-2}$ torr. The approximate layer thickness was 100 Å. Exposed to hydrazine, the surface showed a similar spectrum as observed with the Ag base substrate.

EXAMPLE 5

$NO_2$ Monitor

An $Ag/Ag_2O$ substrate was prepared as in Example 1. On exposure of the surface to $NO_2$, the SERS spectrum exhibits major bands associated with $NO_2$ at 815 and 1285 cm$^{-1}$. The phenomenon is readily reversible, the signal level being proportional to $NO_2$ concentration at room temperature, and the $NO_2$-related bands disappearing when $NO_2$ is removed from the gas stream. Thus, a dynamic physisorptive equilibrium is indicated, which is useful for a renewable sensor which responds with a signal in direct proportion to the vapor phase $NO_2$ concentration.

The substrate and apparatus of the present invention will find widespread use in the detection and analysis of dilute species in air and other gaseous environments. Examples include detection of specific air pollutants, particularly in a background of other pollutants, due to the narrow band width of Raman frequencies characterizing individual molecules as well as the possibility of employing chemically specific surfaces. Other applications include gas monitors for fossil fuel burning plants, distillation column monitors, and medical sensors for digestive disorders.

The description of embodiments encompassing the present invention should not be intended as limiting the scope of the invention, which is defined in the following claims.

TABLE 1

SERS response of gas phase molecules in contact with electrochemically roughened Ag and electrochemically roughened Ag with a subsequently grown Ag oxide.

| Vapor | Ag | Ag/Ag oxide |
|---|---|---|
| Methanol | N | Y |
| Ethanol | N | Y |
| Formaldehyde | N | Y |
| Dimethyl methyl phosphanate (DMMP) | N | Y |
| Hydrazine | N | Y |
| Unsymmetrical dimethyl hydrazine | N | Y |
| Pyridine | Y | N |
| $NO_2$ | N | Y |

TABLE 1-continued

SERS response of gas phase molecules in contact with electrochemically roughened Ag and electrochemically roughened Ag with a subsequently grown Ag oxide.

| Vapor | Ag | Ag/Ag oxide |
|---|---|---|
| $SO_2$ | N | Y |

What we claim is:

1. A substrate for surface enhanced Raman spectroscopy (SERS) of one or more molecular species, comprising
   (a) a SERS-active metal capable of exhibiting a surface enhancement of Raman scattering of said molecular species, and
   (b) a coating deposited by external means on said SERS-active metal and capable of adsorbing or reacting with said molecular species and bringing the adsorbed species or the reaction products in close proximity with said SERS-active metal whereby the Raman spectrum of the said adsorbed species or products may be observed to be enhanced by the SERS-active metal.

2. A substrate according to claim 1 wherein said coating contains said metal dispersed within it as a second phase.

3. A substrate according to claim 2 produced by initially incorporating a compound of said metal in said coating and then exposing the mixture to a reducing agent
   whereby the metal ions of said compound are reduced to form said SERS-active metal dispersion.

4. A substrate according to claim 3 in which said compound is silver oxide, said SERS-active metal is silver, and said reducing agent is hydrazine.

5. A substrate according to claim 1 in which said SERS-active metal is comprised of at least one member selected from the group consisting of: silver, gold, copper, platinum, iridium, gallium, lithium and lead.

6. A substrate according to claim 1 in which said coating is an oxide of said metal, said oxide having a reactive or adsorptive affinity for said molecular species.

7. A substrate according to claim 6 formed by electrochemically roughening said SERS-active metal in a non-oxide forming electrolyte and then electrochemically oxidizing the surface of said roughened metal in an oxide forming electrolyte.

8. A substrate according to claim 6 formed by simultaneously roughening said SERS-active metal and growing an oxide on its surface by electrochemical cycling between voltage limits in an oxide forming electrolyte.

9. A substrate according to claim 1 in which said coating is an organic polymer with a reactive or adsorptive affinity for said molecular species.

10. A substrate according to claim 6 in which said coating is silver oxide and said molecular species is hydrazine or a derivative of hydrazine.

11. A spectroscopy apparatus for sensing one or more molecular species comprising
    (a) a light source producing monochromatic excitation light;
    (b) a substrate for surface enhanced Raman spectroscopy (SERS) of said molecular species, comprising a SERS-active metal capable of exhibiting a surface enhancement of Raman scattering of said molecular species, and a coating deposited by external means on said SERS-active metal and capable of adsorbing or reacting with said molecular species and bringing the adsorbed species or the reaction products in close proximity with said SERS-active metal (c) optical means for directing said monochromatic excitation light onto said substrate or portion thereof and for collecting said Raman scattered light from said substrate or portion thereof;

(d) spectrometric means for producing an electronic signal proportional to the intensity of said Raman scattered light in a fixed wavelength range or as a function of wavelength;

whereby said electronic signal at wavelengths characteristic of said adsorbed molecular species or said reaction products thereof is used to identify said molecular species and/or to specify the concentration of said molecular species.

12. An apparatus according to claim 11, further comprising a mechanical means for exposing said substrate to a gas stream containing said molecular species.

13. An apparatus according to claim 11 wherein said molecular species is hydrazine and hydrazine derivatives or mixtures thereof
wherein said substrate is comprised of silver metal and silver oxide coating.

14. An apparatus according to claim 11 wherein said molecular species is comprised of ethanol in mixtures of other gases and
wherein said substrate is comprised of gold metal and gold oxide coating.

15. An apparatus according to claim 11 in which said spectrometric means is comprised of one or more light filters with a net effect of passing only wavelengths associated with said Raman scattered light of said molecular species and a photoelectric means for detecting the intensity of said light and for producing said electronic signal.

16. An apparatus according to claim 11, further comprising a piezoelectric crystal on which said substrate is deposited.
whereby the mass of said adsorbed species may be determined from the vibrational frequency of said crystal and the identity of said adsorbed species may be determined from the SERS spectrum.

* * * * *